US005998192A

United States Patent [19]

Russell et al.

[11] Patent Number: 5,998,192

[45] Date of Patent: *Dec. 7, 1999

[54] DELIVERY OF NUCLEIC ACIDS

[75] Inventors: Stephen James Russell, Rochester, Minn.; Francois-Loic Cosset, Lyons, France; Frances Joanne Bullough, Cambridge, United Kingdom; Robin Anthony Weiss; Mary Katharine Levinge Collins, both of London, United Kingdom

[73] Assignee: Medical Research Council, London, United Kingdom

[ * ] Notice: This patent is subject to a terminal disclaimer.

[21] Appl. No.: 08/914,828

[22] Filed: Aug. 19, 1997

Related U.S. Application Data

[63] Continuation-in-part of application No. 08/765,512, filed as application No. PCT/GB95/01506, Jun. 27, 1995, Pat. No. 5,858,743.

[30] Foreign Application Priority Data

Jun. 27, 1994 [GB] United Kingdom .................. 9412844

[51] Int. Cl.[6] .............................. C12N 7/00; C12N 15/86; C12N 5/00; C07H 21/04

[52] U.S. Cl. ........................ 435/235.1; 435/325; 435/456; 536/23.1

[58] Field of Search ......................... 435/6, 235.1, 320.1, 435/325, 456, 235; 536/23.1

*Primary Examiner*—Nancy Degen
*Assistant Examiner*—William Sandals
*Attorney, Agent, or Firm*—Banner & Witcoff, Ltd.; Kathleen M. Williams

[57] ABSTRACT

The invention relates to a recombinant viral particle capable of delivering a nucleic acid to mammalian cells, the particle including a member of a first specific binding pair capable of binding to a first receptor expressed on the surface of a cell so as to cause infection thereof, and a surface-exposed member of a second specific binding pair capable of binding to a second receptor generally not expressed on the surface of the cell, such that binding of the viral particle to the second receptor via the member of the second specific binding pair inhibits infection of the cell by the viral particle.

19 Claims, 6 Drawing Sheets

SEQUENCE LISTING

```
(1) GENERAL INFORMATION:

   (iii) NUMBER OF SEQUENCES:2


(2) INFORMATION FOR SEQ ID NO: 1:

     (i) SEQUENCE CHARACTERISTICS:
          (A) LENGTH: 60 base pairs
          (B) TYPE: nucleic acid
          (C) STRANDEDNESS: single
          (D) TOPOLOGY: linear

    (xi) SEQUENCE DESCRIPTION: SEQ ID NO: 1:

ATGCTCAGAG GGGTCAGTAC GGCCCAGCCG GCCATGGCCA ATAGTGACTC TGAATGTCCC      60


(2) INFORMATION FOR SEQ ID NO: 2:

     (i) SEQUENCE CHARACTERISTICS:
          (A) LENGTH: 50 base pairs
          (B) TYPE: nucleic acid
          (C) STRANDEDNESS: single
          (D) TOPOLOGY: linear

    (xi) SEQUENCE DESCRIPTION: SEQ ID NO: 2:

ACCTGAAGTG GTGGGAACTG CGCGCGGCCG CATGTGGGGG TCCAGACTCC                50
```

DELIVERY OF NUCLEIC ACIDS

This is a continuation-in-part application of U.S. Ser. No. 08/765,512 filed Jun. 9, 1997, now U.S. Pat. No. 5,858,743.

FIELD OF THE INVENTION

The invention relates to viral particles capable of delivering nucleic acids, compositions comprising such viral particles, and to methods of altering the host cell range of such viruses.

BACKGROUND OF THE INVENTION

Retroviral vectors derived from C-type murine leukaemia viruses (MLVs) have emerged as highly versatile gene delivery vehicles and have been selected for use in many human gene therapy protocols, especially those requiring transduction of normal or neoplastic haemopoietic cells. In the interests of safety and efficacy, particularly for direct genetic modification of target cells in vivo, it is desirable that retroviral gene delivery should be accurate but the clinically approved (amphotropic) retroviral vectors in current use attach to an ubiquitously expressed cellular receptor and therefore infect human cells promiscuously. Cell-selective retroviral gene delivery might be achieved by modification of the viral membrane spike glycoproteins responsible for receptor-mediated virus entry.

SUMMARY OF THE INVENTION

In a first aspect, the invention provides a recombinant viral particle capable of delivering a nucleic acid to mammalian cells, the particle comprising a member of a first specific binding pair capable of binding to a first receptor expressed on the surface of a cell so as to cause infection thereof, and a surface-exposed member of a second specific binding pair capable of binding to a second receptor generally not expressed on the surface of the cell, such that binding of the viral particle to the second receptor via the member of the second specific binding pair inhibits infection of the cell by the viral particle.

"Delivery" as used herein, is intended to mean the entry of a nucleic acid, essentially intact (i.e. without substantial loss of information content), into the interior (preferably the nucleus) of a cell.

Preferably, the recombinant viral particle is a retrovirus, typically an MLV, which have been extensively studied as gene delivery systems.

It will be apparent that whilst one member of the first specific binding pair ("sbp") is provided on the particle, the first receptor molecule expressed on the surface of the cell represents the other member of the first sbp. The term "sbp" should not be taken to mean that the members of the sbp cannot necessarily bind to other molecules, but that there is an interaction between the members of the pair. Similarly, whilst the member of the second sbp is provided (on the surface) of the viral particle, the second receptor on the cell surface represents the other member of the second sbp.

Advantageously, the member of the first sbp, provided on the viral particle, will be the normal ligand by which the virus infects host cells and the other member of the first step being the normal receptor by which the virus infects host cells. An example of a suitable member of an sbp include the retroviral env protein, or an effective portion thereof sufficient to mediate binding to, and infection of, a host cell.

Generally, the second receptor is not expressed on the cell to which the nucleic acid is to be desirably delivered (but may be expressed at a low level, or at certain stages of the cell's life cycle). Preferably the second receptor will not be expressed at all on the cell to which the nucleic acid is desirably to be delivered. In this way, the viral particle will tend to bind to the desired target cell by way of the interaction between the members of the first sbp. Other cells (to which the nucleic acid is preferably not delivered) may also be present and may express the first receptor, but will advantageously express the second receptor also, thereby allowing the viral particle to bind to such cells without causing infection thereof (thus preventing effective delivery of the nucleic acid to such cells).

Conveniently, the member of the second sbp provided on the virus may be expressed as a fusion with the member of the first sbp.

Preferably the member of the second sbp provided on the surface of the particle is human EGF, which will bind with high affinity to the EGF receptor, which is expressed on many different human cell types.

Preferably the interaction between the members of the second sbp is one with a high affinity (with equilibrium constants of $10^{-8}$M or lower).

Advantageously, the member of the second sbp is such that the other member of the second sbp (i.e the second receptor) is a receptor expressed by cells which are capable of migration within the human body.

In a further aspect, the invention provides a composition comprising a recombinant viral particle as defined above, and one or more cells to which the nucleic acid is capable of being delivered.

Preferably, the composition comprises haemopoietic cells, typically leukocytes and the like. Typically the composition will comprise one or more cells (to which the nucleic acid is desirably delivered) which express the first receptor but not the second receptor, and one or more cells (to which the nucleic acid is preferably not delivered) which express both the first receptor and the second receptor.

It will be apparent from the foregoing that, in a further aspect, the invention also provides a method of restricting the host range of a viral particle, the viral particle comprising a member of a first specific binding pair capable of binding to a first receptor expressed on the surface of a cell so as to cause infection thereof, the method comprising causing to be present on the surface of the viral particle a member of a second specific binding pair capable of binding to a second receptor molecule expressed on the surface of a subset of the cell population which are hosts for infection by the virus, such that binding of the viral particle to the second receptor molecule, via the member of the second specific binding pair, inhibits infection of the cell by the viral particle.

The present inventors have also surprisingly found that exogenously added substances can extend the host range of a viral particle. Thus, in a further aspect the invention also provides a method of extending the host range of a viral particle comprising a nucleic acid capable of being delivered to a target cell, the method comprising causing to be present on the surface of the viral particle a member of a specific binding pair capable of binding to a cell surface receptor, the binding reaction not generally facilitating infection of the cell by the virus, but so facilitating in the presence of an exogenously added substance.

Preferably, the method is performed on a viral particle which is not normally capable of infecting mammalian cells, or not normally capable of infecting a particular mammalian cell type, or which does so only very inefficiently.

One suitable exogenous substance is chloroquine. Chloroquine is known to interfere with lysosomal activity, and it is quite possible that this is the route by which chloroquine exerts its presently identified effect. Thus, other substances which also interfere with lysosomal activity may represent suitable alternatives. Identification of alternative substances will be a matter of routine for those skilled in the art, with the benefit of the teaching of the present specification.

Further features and advantages of the invention will become more fully apparent in the following description of the embodiments and drawings thereof, and from the claims.

BRIEF DESCRIPTION OF THE DRAWINGS

The invention will now be further described by way of illustrative example and with reference to the drawings, of which.

DESCRIPTION

Figure 1A:
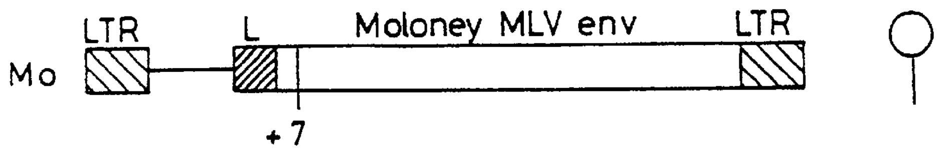
FIG. 1 is a schematic representation of various wild type and chimaeric retrovirus envelope constructs; (EGF=epidermal growth factor, L=Leader signal sequence from Moloney MLV env; all env genes were expressed using the same promoter, the Friend MLV long terminal repeat "LTR", codon numbering refers to distance from N-terminus of mature SU glycoprotein)
Figure 1B:
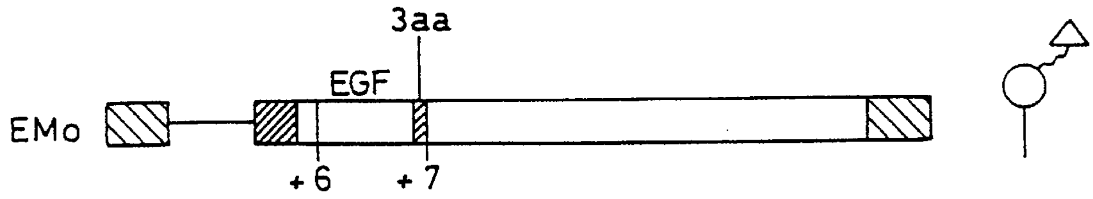
Figure 1C:
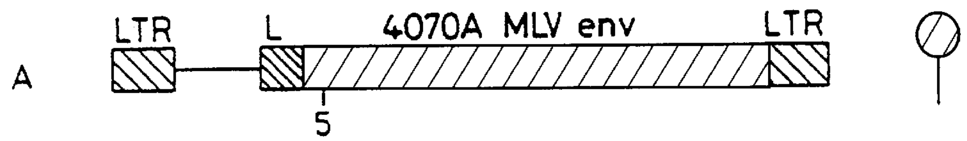
Figure 1D:
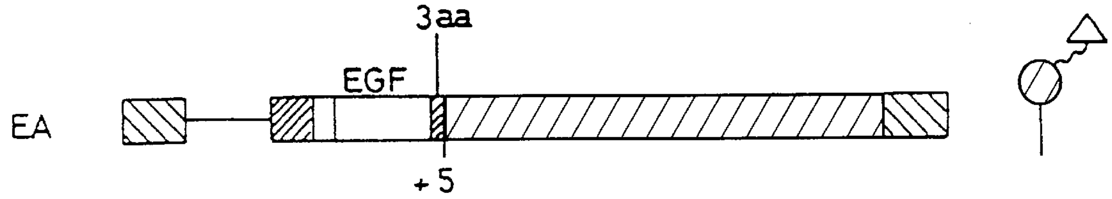

The invention provides a method of restricting the host range of a viral particle. The viral particle includes a member of a first specific binding pair capable of binding to a first receptor expressed on the surface of a cell so as to cause infection thereof. The method includes causing to be present on the surface of the viral particle a member of a second specific binding pair capable of binding to a second receptor molecule expressed on the surface of a subset of the cell population which are hosts for infection by the virus, such that binding of the viral particle to the second receptor molecule, via the member of the second specific binding pair, inhibits infection of the cell by the viral particle.

This method of the invention is particularly suitable for increasing the specificity of effective delivery of a nucleic acid, such that the nucleic acid may, or may not, enter a wide variety of cell types, but will only be efficiently delivered and expressed in a particular subset of the total cell population to which the viral particle is capable of binding.

The invention provides a recombinant viral particle capable of delivering a nucleic acid to mammalian cells, the particle comprising a member of a first specific binding pair capable of binding to a first receptor expressed on the surface of a cell so as to cause infection thereof, and a surface-exposed member of a second specific binding pair capable of binding to a second receptor generally not expressed on the surface of the cell, such that binding of the viral particle to the second receptor via the member of the second specific binding pair inhibits infection of the cell by the viral particle. The invention also provides this recombinant viral particle, and one or more cells to which the nucleic acid is capable of being delivered. The elements of the invention, i.e., a "member of a first specific binding pair capable of binding to a first receptor", a "first receptor", a "surface-exposed member of a second specific binding pair capable of binding to a second receptor", a "second receptor", and cells to which the nucleic acid may be delivered, are described in detail below.

According to the invention, the member of the first sbp (provided on the viral particle) may be the normal ligand by which the virus infects host cells and the other member of the first step may be the normal receptor by which the virus infects host cells; for example, the retroviral env protein (or an effective portion thereof sufficient to mediate binding to, and infection of, a host cell), and the host cell receptor for the env protein.

Generally, the second receptor is not expressed on the cell to which the nucleic acid is to be desirably delivered (but may be expressed at a low level, or at certain stages of the cell's life cycle, or may not be expressed at all). In this way, the viral particle will tend to bind to the desired target cell by way of the interaction between the members of the first sbp.

Retroviral envelope glycoproteins mediate specific viral attachment to cell surface receptors and subsequently trigger fusion between the viral envelope and the target cell membrane. Retroviral envelope glycoproteins consist of an external glycoprotein moiety (SU) noncovalently attached at its C-terminus to a smaller transmembrane polypeptide moiety (TM). Each surface projection (or spike), visible by electron microscopy on the viral surface is a trimer of identical envelope glycoprotein subunits. SU comprises two domains connected by a proline-rich hinge, the N-terminal domain conferring receptor specificity and exhibiting a high degree of conservation between MLV's with different host ranges (Battini et al, 1992 J Virol 66 p1468–1475).

The crystallisation of retroviral SU proteins or their domains remains elusive but sequence alignment of the SU receptor-binding domains of C-type retroviruses reveals a high degree of homology, presumably reflecting a conserved 3-dimensional fold. Two discontinuous hypervariable peptide sequences in this domain, VRA and VRB, have been identified as major determinants of receptor-binding specificity (Battini et al, 1995 J Virol 69 p713–719). Thus it is probable that these receptor binding domains consist of a conserved framework acting as a scaffold for presentation of hypervariable peptide loops which confer binding specificity. According to the "canyon hypothesis", the receptor binding site in SU is likely to take the form of a pocket or groove whose walls and floor may be formed by the residues in VRA and VRB.

Retroviral host range is determined in part by the species and tissue distribution of specific cell surface receptors that are recognised by the viral envelope glycoprotein. Moloney MLV is an ecotropic virus whose envelope attaches to mouse and rat cells but not to human cells. 4070A MLV is an amphotropic virus whose envelope attaches to cells of mouse and human origin. Three C-type retrovirus receptors have now been identified and all are membrane permeases with multiple membrane-spanning domains. In the case of Moloney MLV, the precise target for virus attachment is a constrained peptide loop in the third extracellular domain of the murine cationic amino acid transporter (CAT1) which also functions as a Moloney virus receptor when transplanted into the corresponding site on a homologous human protein (Albritton et al, 1993 J Virol 67 p2091–2096).

Naturally occurring retroviruses incorporate a single species of envelope glycoprotein which mediates specific high-affinity binding to a single well-defined cognate cell-surface receptor. However, additional receptor-binding domains can be incorporated to generate retroviral particles that are capable of binding to more than one species of cellular receptor. Thus, with dual viral infection of a single cell by two enveloped viruses, the host range of either virus may be predictably extended due to promiscuous incorporation of spike glycoproteins encoded by both viruses (Levy, 1976 Virology 77 p811–825; Weiss & Wong, 1977 Virology 76 p826–834; Besmer & Baltimore, 1977 J Virol 21 p965–973; Canivet et al, 1990 Virology 178 p543–541; Lusso et al, 1990 Science 247 p848–852; Spector et al, 1990 J Virol 64 p2298–2308; Schnitzer et al, 1977 J Virol 23 p449–454; Metsikko & Garoff, 1989 J Virol 63 p5111–5118; Schubert et al, 1992 J Virol 66 p1579–1589).

Non-viral polypeptide ligands can also be co-incorporated (or pseudotyped) into retroviral vectors with unmodified retroviral envelope glycoproteins. Thus, MHC antigens are incorporated into the envelopes of human and simian immunodeficiency viruses (Gelderblom et al, 1987 Z Naturforsch 42 p1328–1334; Schols et al, 1992 Virology 189 p374–376) mammalian CD4 expressed in avian (quail) cells was incorporated into the envelopes of budding avian retroviruses (Young et al, 1990 Science 250 p1421–1423), a CD4-envelope chimaera, retaining the membrane anchor sequence of the retroviral envelope glycoprotein, was co-incorporated into avian retroviruses with wild type avian retroviral envelope glycoproteins (Young et al, 1990 Science 250 p1421–1423) and a single chain antibody/envelope chimaera was similarly co-incorporated into avian retroviruses (Chu & Dornberg, 1995 J Virol 69 p2659–2663). In the latter example, the host range of the retroviruses was extended to otherwise non-permissive cells that express the tumour antigen recognised by the displayed single chain antibody. A chimaeric Moloney MLV envelope glycoprotein in which the N-terminal domain of SU had been substituted by erythropoietin was co-incorporated into MLV particles with unmodified Moloney envelope glycoprotein (Kasahara et al, 1994 Science 266 p1373–1376). In this example, the authors claimed that the host range of the erythropoietin-displaying viruses was extended to human cells expressing the erythropoietin receptor and that their infectivity was enhanced on mouse fibroblasts that had been transfected with an expression vector coding for erythropoietin receptor. Non-viral polypeptide ligands have also been displayed on retroviruses as N-terminal extensions of a substantially intact Moloney MLV retroviral envelope glycoprotein which retains its receptor-binding domain (Russell et al, 1993 NAR 21 p1081–1085).

In summary, several non-viral polypeptide ligands have been co-incorporated into retroviral vectors with unmodified envelope proteins. The purpose of these manipulations has been to selectively enhance the infectivity of the recombinant retroviruses for cells expressing receptors that are recognised by the non-viral ligand. Selective inhibition of retroviral entry into cells expressing receptors for a displayed non-viral ligand has not previously been proposed, observed or discussed.

According to the invention, the member of the second sbp provided on the virus may be expressed as a fusion with the member of the first sbp. Conveniently, the member of the second sbp will be provided as a fusion at (or near) the N or C terminal of the member of the first sbp. A particularly suitable insertion site, allowing for N-terminal fusion, is known for the retroviral env protein (Russell et al., 1993 N.A.R. 21, 1081–1085). Other suitable fusion sites will be apparent to those skilled in the art.

In a preferred embodiment, the member of the second sbp provided on the surface of the particle is human EGF, which will bind with high affinity to the EGF receptor, which is expressed on many different human cell types. The present inventors found that binding to the EGF receptor inhibited the ability of viral particles to infect cells. Those skilled in the art will recognise that a number of other molecules may constitute appropriate second specific binding pairs. Use of the methods described herein will allow the identification of other cell surface receptors which tend to inhibit viral infection. In particular, other specific binding pairs may comprise growth factors/growth factor receptors. Numerous growth factors are given, for example, in WO 94/27643 (Targeted Genetics Corporation). Other appropriate second receptors might be molecules which, in the case of enveloped viruses, interfere with fusion between the viral and host cell envelopes.

It is preferred that the interaction between the members of the second sbp is one with a high affinity (with equilibrium constants of $10^{-8}$M or lower). This has the advantage that, where a particular cell expresses both the first and the second receptors, binding of the viral particle to the cell via the second receptor will be favoured relative to binding via the first receptor. This allows for greater specificity of targeting for delivery of the nucleic acid by the viral particle, such that effective delivery of the nucleic acid will tend to take place only to those cells which express the first receptor and not the second receptor (nor cells on which the second receptor is expressed only at very low levels).

Advantageously, the member of the second sbp is such that the other member of the second sbp (i.e the second receptor) is a receptor expressed by cells which are capable of migration within the human body. Such cells include haemopoietic cells and transformed cells (generally detached from tumours, which can lead to metastases). This allows for the viral particle to bind to the migratory cells without infection thereof, such that the viral particles may be carried to particular sites within the body (e.g. sites of tumour growth or metastases). Once at these sites, the viral particles, still attached to the surface of the migratory cells (via the interaction between the members of the second sbp), may then bind to other cells (via the interaction between the members of the first sbp) so as to cause infection thereof, leading to effective delivery and subsequent expression of the nucleic acid. In this particular embodiment the delivered nucleic acid may typically encode polypeptide(s) which will tend to inhibit tumour growth, such as MHC or other antigens (increasing susceptibility to immune responses), anti-angiogenic factors, tumour necrosis factor and the like.

The invention is illustrated by the following nonlimiting examples wherein the following materials and methods are employed. The entire disclosure of each of the literature references cited hereinafter are incorporated by reference herein.

EXAMPLES

In an attempt to target retroviral gene delivery through the human epidermal growth factor receptor (EGFR) to EGFR-positive cells, the inventors constructed a chimaeric envelope construct in which the human EGF coding sequences were cloned, in frame, into a SfiI - NotI cloning site which had been introduced between the 6th and 7th codons of the env gene of Moloney MLV (Russell et al, 1993 Nucleic Acids Research 21, 1081–1085; Russell et al, PCT/GB93/01992). This chimaeric envelope construct (EMO) was then transfected into the complementing cell line TELCeB6 which expresses MLV gag and pol functions and a packagable RNA transcript coding for β-galactosidase. The transfected TELCeB6 cells released retroviral particles which efficiently incorporated the chimaeric EMO envelope glycoprotein, as shown by western blot analysis of pelleted virus. Viruses incorporating the chimaeric EMO envelope glycoprotein were shown by chromogenic substrate assay to transfer the β-galactosidase gene to mouse NIH3T3 cells, indicating that the chimaeric protein could still bind to the ecotropic MLV receptor and catalyse membrane fusion.

Viruses incorporating the chimaeric EMO envelope glycoprotein were then separated from soluble (shed) envelope glycoprotein by sephacryl column chromatography of 0.45 μM-filtered culture supernatant and were shown by immunofluorescence staining to bind efficiently to EGF.R-positive human cell lines (i.e. cell lines expressing EGF receptor). Binding to these cells was competitively inhibited by soluble EGF. However, the bound virus did not transfer a functional β-galactosidase gene to the human cell lines, whereas control viruses incorporating the amphotropic 4070A envelope efficiently transferred the β-galactosidase gene to these same human cell lines.

The inventors next examined the efficiency of gene transfer to EGFR-positive human cells using recombinant retroviruses displaying the EGF polypeptide fused to the amphotropic 4070A envelope glycoprotein. The chimaeric EGF-4070A (EA) expression construct was created by substituting most of the MoMLV env sequence in FBEGFMosA (from codon 7, immediately 3' of the NotI cloning site to the ClaI site close to the 3' end of the env gene) for corresponding 4070A env sequence (from codon 5 to the ClaI site close to the 3' end of the env gene).

Recombinant retroviruses displaying the chimaeric EA envelope protein behaved in an unexpected fashion. They transferred the β-galactosidase gene efficiently to mouse NIH3T3 cells and to human cells that were negative for EGF receptor expression, but not to EGF receptor-expressing human cells. The titre reduction on EGF receptor-positive human cells was as much as ten million-fold compared to control viruses incorporating unmodified 4070A amphotropic envelopes.

Subsequent experiments using various target cells of mouse and human origin, some of which had been transfected with an EGFR expression plasmid, proved that viruses displaying the chimaeric EMO and EA envelope glycoproteins had selectively impaired ability to infect ecotropic or amphotropic MLV receptor-positive cells that also expressed EGF receptors. Higher levels of EGF receptor expression were associated with greater impairment of infectivity. Cells transfected with an EGF receptor expression plasmid became selectively resistant to EMO and EA viruses, and this resistance was reversible upon treating the cells with soluble EGF to block/downregulate the EGF receptors. Thus, retroviral host range was selectively restricted to EGF receptor-negative cells by displaying a high affinity ligand for EGF receptors on the viral surface.

The present inventors have thus discovered a novel biological phenomenon which they have called ligand-dependent, receptor-mediated viral sequestration—a method by which to restrict the host range of a MLV or MLV-based retroviral vector in a ligand-dependent fashion. The first step is to identify a polypeptide ligand which binds specifically to a cell surface marker present on nontarget cells but absent from the target cell population. This polypeptide is then fused (by genetic engineering) to the retroviral envelope protein such that the envelope protein to which it has been grafted remains substantially intact and capable of binding to its natural receptor, and the fused nonviral polypeptide ligand is displayed on the viral surface. The virus displaying the fused nonviral polypeptide ligand is then capable of multivalent attachment to the natural virus receptor and to the cognate receptor for the nonviral ligand; attachment to the natural virus receptor leads to infection of the target cell, whereas attachment to the cellular receptor for the displayed nonviral ligand may not lead to infection of the target cell. Where the target cell expresses both species of receptor and attachment through the displayed nonviral ligand does not lead to infection, the two binding reactions (envelope protein to natural receptor and nonviral ligand to its cognate receptor) proceed in competition and the infectivity of the virus for the target cells is reduced in proportion to the efficiency with which the second binding reaction competes virus away from the natural virus receptor.

The degree to which gene transfer is inhibited will therefore be influenced by the relative affinities of the two binding reactions, the relative densities of the two receptors on the target cell surface, and the relative densities of the non-viral ligand and the intact envelope protein on the viral surface. Inhibition of gene transfer is additionally influenced by intrinsic properties of the receptor for the non-viral ligand, such as the distance it projects from the target cell membrane, its mobility within the target cell membrane and its half life on the cell surface after engagement of ligand. This method of host range restriction may be applicable to the membrane spike glycoproteins of other enveloped viruses, and to the attachment proteins of non-enveloped viruses such as the adenovirus fibre protein. Where an enveloped virus has multiple distinct membrane spike glycoproteins with differing binding specificities and fusogenic capabilities (eg paramyxiviridae, herpesviridae), the restriction of virus host range by this method may or may not require the modification of more than one of the glycoproteins.

The invention offers a novel strategy for targeting retroviral gene delivery by host range extension. After binding to its receptor, EGF is endocytosed and routed to lysosomes, where EGF—EGF receptor complexes are degraded (Carpenter & Cohen, 1990 J Biol Chem 265 p7709–7712). The inventors suspected that viruses bound to EGF receptors might therefore also be rapidly endocytosed and routed to lysosomes for degradation. The inventors therefore attempted to rescue EMO-carrying viral particles from this degradative pathway by treating infected human cells with chloroquine phosphate, a lysosomotropic base which inhibits lysosomal acidification. Viruses carrying unmodified Moloney envelopes (which do not bind efficiently to human cells) were unable to infect the human cell lines, irrespective of the presence of chloroquine. In contrast, viruses carrying EMO envelopes which were shown to bind efficiently to EGF receptors on human cells showed significant infectivity on human EGF receptor-positive cells in the presence of chloroquine. In contrast, there was no evidence of infection in the presence of chloroquine on EGF receptor negative K422 B cells, to which the EMO virus did not bind.

This novel approach to viral host range restriction could have useful applications in the fields of gene therapy and virotherapy. Prevention of gene delivery to selected non-target cells may be advantageous for reasons of safety or efficacy in many human gene therapy protocols. For example, certain therapeutic genes (eg cytokines, drug resistance markers, drug sensitivity markers) may have deleterious effects when expressed in non-target cells. The development of replicating vectors for tumour cell-targeted gene therapy or virotherapy will also require reliable strategies for restricting virus host range. The method might also be used to enhance the safety of viruses which are used for the control of agricultural pests, by restricting their tropism to a single species of pest.

Example 1

Construction of chimaeric retroviral envelopes

The sequence coding for EGF (epidermal growth factor) was inserted in MLV (murine leukemia virus) env gene in a position corresponding to amino-acid +6 in the SU glycoprotein of MoMLV (FIG. 1). This position of insertion was previously shown to allow the functional display of single chain antibodies at the surface of virions (Russell et al, 1993 NAR 21 p1081–1085). The EGF domain was separated from the wild type receptor binding domain in the envelope by a small linker containing 3 alanine residues. In the chimera EMO, EGF was inserted in the Mo-MLV envelope, whereas chimera EA had an EGF insertion in the MLV amphotropic (4070A) envelope at position +5. Envelopes, including the control envelopes from ecotropic (MO) and amphotropic (A) MLV, were transfected into TELCeB6 cells which express MLV gag-pol core particles and a lacZ retroviral vector.

Expression and viral incorporation of chimaeric envelopes

Figure 2:
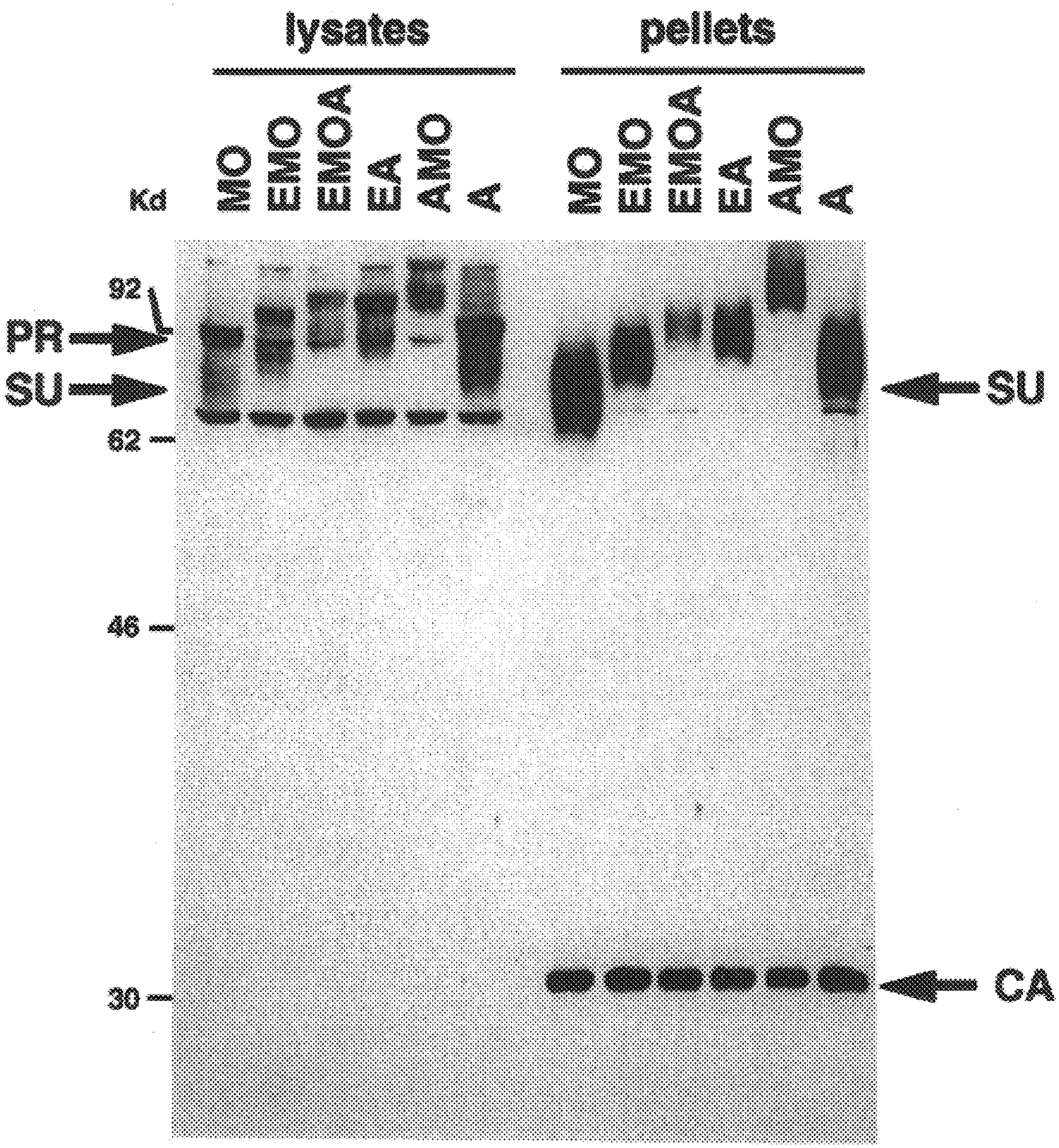
FIG. 2 is a picture of Western blots, showing detection of envelope SU proteins; immunoblots of lysates (on the left) of TELCeB6 cells transfected with the envelopes shown in FIG. 1 or of pellets (on the right) of viral particles produced from these cells. Both blots were stained with an SU anti-serum. The immunoblot of pellets was cut at 46 kD, and the lower part was stained with a p30-CA anti-serum.

Lysates of TELCeB6 cells were analysed for envelope expression using antibodies against MLV SU (FIG. 2). For both chimeric envelopes, both a precursor and a processed SU product were detected at ratios similar to wild-type envelopes, suggesting that the mutants were correctly expressed and processed. Cell surface expression of mutant envelopes was examined by FACS analysis of producer cells, using antibodies against the SU or a monoclonal anti-hEGF antibody. All transfected cells were stained with the anti-SU antibodies, and cells expressing the EGF-fusion envelopes were stained with anti-EGF monoclonals (data not shown).

To demonstrate incorporation of the chimeric envelope glycoproteins into retroviral particles, supernatants of the various TELCeB6-transfected cell lines were ultracentrifuged to pellet viral particles. Pellets were then analysed on immunoblots for their content of gag (p30-CA) and envelope proteins (FIG. 2). The chimaeric SU glycoproteins were detected at a similar ratio to gag compared to wild-type envelope.

Binding of chimaeric envelopes to EGF receptors

Human cell lines expressing different numbers of EGF receptors (FIG. 3 bottom) were used for binding assays. Cells were incubated with virus supernatants and binding of viral envelopes to the target cell surface was analysed by FACS using antibodies against the MLV SU.

MoMLV-derived EGF-fusion envelopes (EMO envelopes) were found to bind to A431 cells (FIG. 3 top) over-expressing EGF.R (FIG. 3 bottom). Less binding was found on TE671 and HT1080 target cells which express less EGF.R (FIG. 3). No binding could be detected on K422 lymphoma cells with no detectable expression of EGF receptor (FIG. 3). The EA envelopes bound to A431 cells as well as EMO (data not shown). EGF receptors on A431 cells were down-regulated by pre-incubation with EGF. This treatment did not affect the binding of amphotropic envelopes (FIG. 4 bottom) but abolished binding of EMO envelopes (FIG. 4 top).

Figure 5:
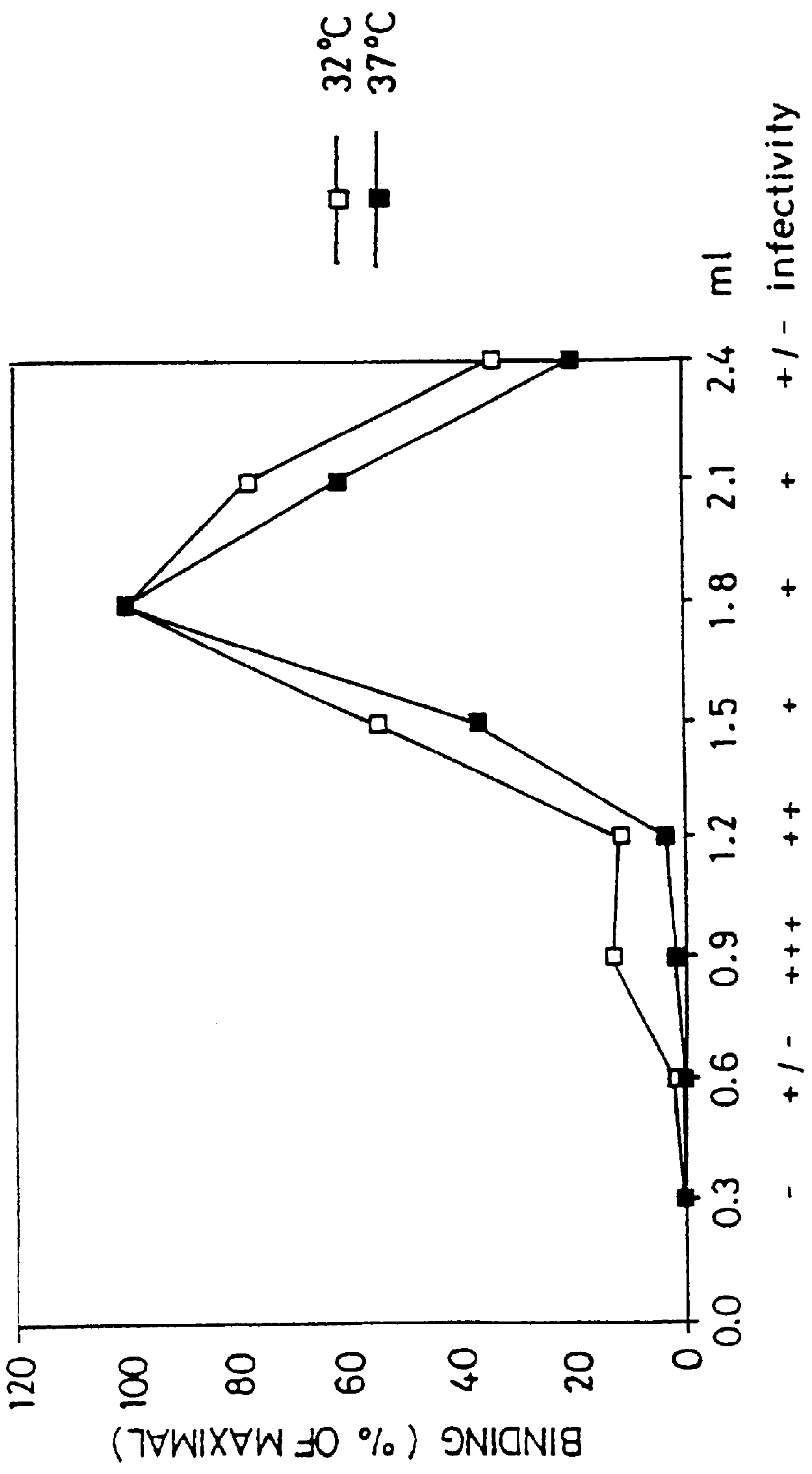
FIG. 5 is a graph showing EGF binding of various fractions (see text) after S-1000 chromatography. Each fraction was analysed both for its binding activity using A431 cells as targets and for infectivity on 3T3 cells: (−): no infectivity, (+/−): 1–10 lacZ-EFU, (+): 10–100 lacZ-EFU, (++): 100–1000 lacZ-EFU, (+++): >1000 lacZ-EFU.

SU envelope glycoproteins of MLVs are known to be weakly associated with their TM protein counterparts (Gliniak et al, 1991 J Biol Chem 266 p22991–22997) and a very low proportion of SU is retained on virions. Therefore it is likely that binding assays in FIG. 3 are due in part to soluble envelope glycoproteins shed from virions. To determine whether viral particles could also bind, the supernatant of producer cells was separated by gel-filtration and fractions were analysed for binding activity on A431 cells (FIG. 5). As expected very little binding activity was found in the early fractions containing the viral particles, with most of the binding activity in the late fractions containing soluble envelopes. However when viral particles were produced at 32° C. in order to reduce the dissociation between SU and TM a significant binding activity was also found in the fractions containing the virions (FIG. 5), demonstrating that viral particles could bind EGF.R.

Host range properties of viruses carrying EMO envelopes

Table 1A shows that viruses incorporating EMO envelopes can infect NIH3T3 mouse fibroblasts. Infection is through the ecotropic MLV receptor because the EMO virus cannot infect NIH3T3 cells expressing the Moloney envelope glycoprotein but can infect those expressing the 4070A envelope glycoprotein. Viruses incorporating EMO envelopes can not only bind to EGF receptors but can also bind and infect cells through ecotropic MLV receptors.

Figure 3A:
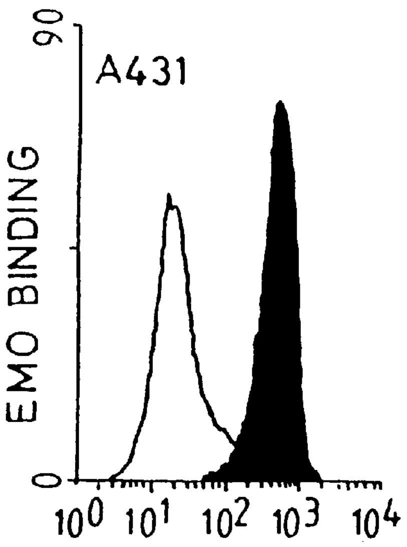
FIG. 3 shows a series of graphs produced by fluorescence-activated cell sorting (FACS), illustrating the results of EGF receptor binding assays; cells were A431, HT1080, TE671, or K422. The top row shows binding assays performed using EMO envelopes (black histograms) compared to MO envelopes (white histograms), whilst the bottom row shows the results when the cells were stained with an anti-hEGF.R antibody.
Figure 3B:
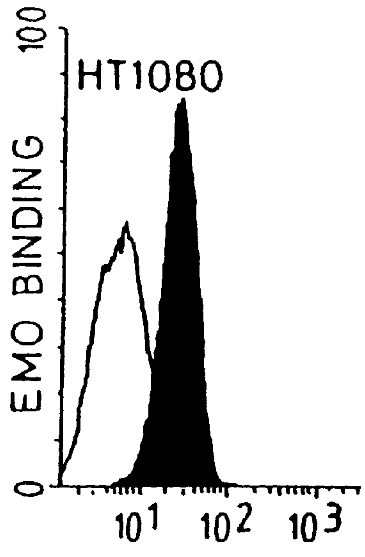
Figure 3C:
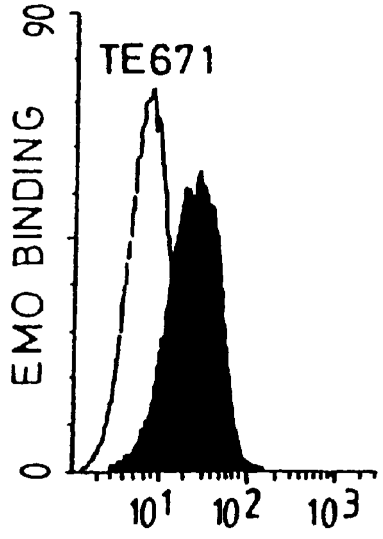
Figure 3D:
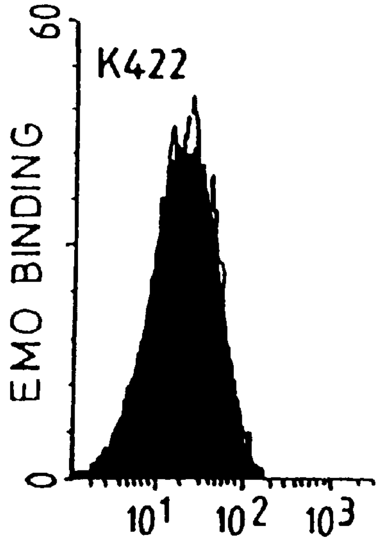
Figure 3E:
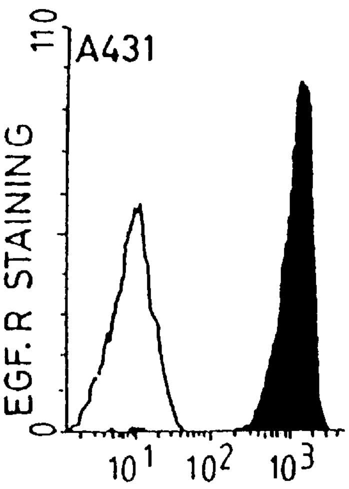
Figure 3F:
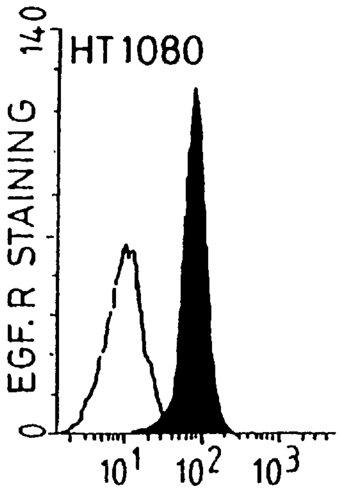
Figure 3G:
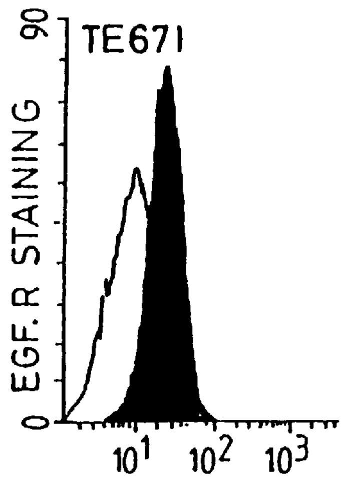
Figure 3H:
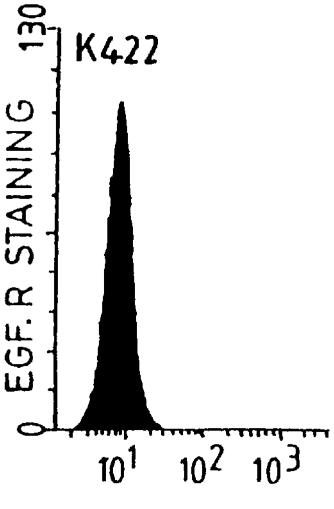
Figure 4A:
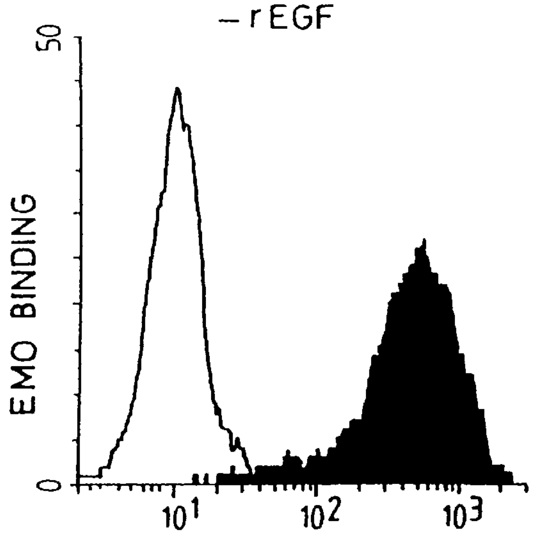
FIG. 4 shows a series of graphs, produced by FACS, illustrating the specificity of EGF binding; A431 cells were used as target cells. Cells were (+rEGF) or were not (−rEGF) treated with recombinant EGF ($10^{-6}$ M, 30 min, 37° C.) prior to binding assays using EMO (top row of graphs) or A envelopes (bottom row)
Figure 4B:
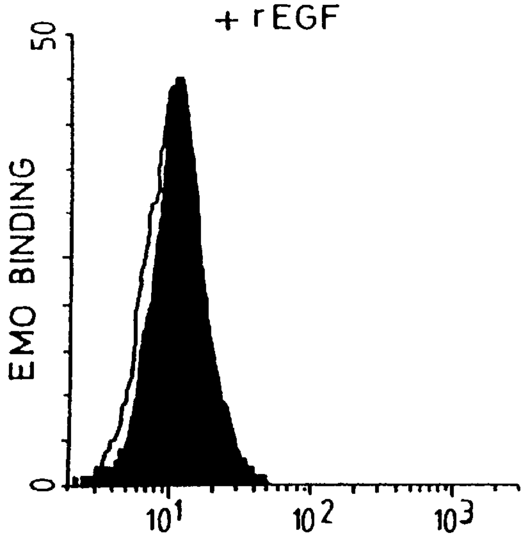
Figure 4C:
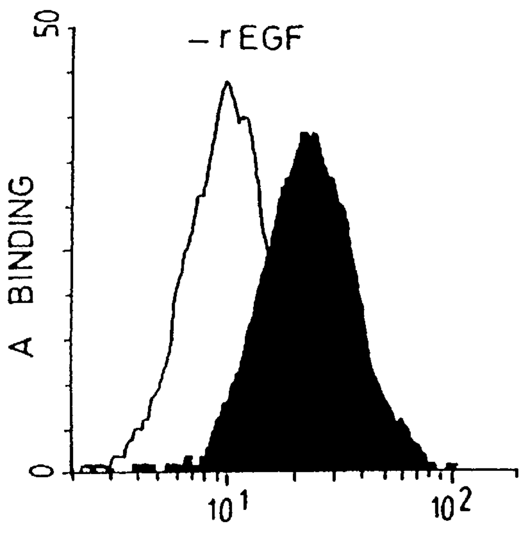
Figure 4D:
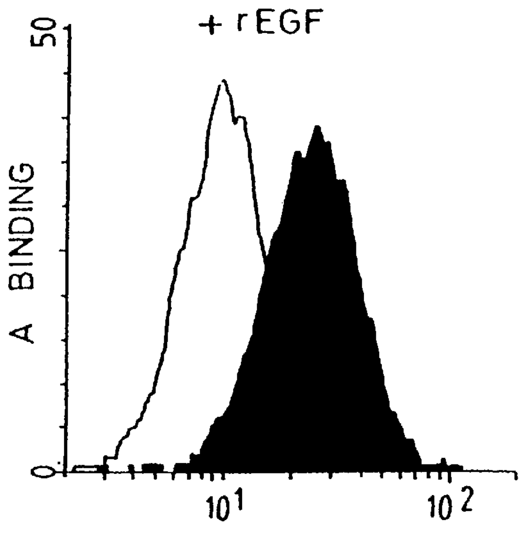

Table 1B shows that viruses incorporating EMO envelopes could not infect human cells expressing various densities of EGF receptors, despite their ability to bind to the EGF receptors on these cells (FIG. 3A). Surprisingly, the cell line EJ.A1, which stably expresses ecotropic MLV receptors from a transfected plasmid, could not be infected by the EMO virus, but was readily infected by viruses incorporating unmodified MO envelopes. This result suggested that the EMO virus could be competitively sequestered by EGF receptors on EJ.A1 cells, preventing it from binding to the ecotropic viral receptors.

Competitive sequestration of viruses carrying EMO envelopes

To test the idea that EMO viruses could be competitively sequestered by EGF receptors at the surface of an otherwise permissive target cell, we titrated viruses incorporating EMO or MO envelopes on mouse fibroblasts (NR6 and NIH3T3) expressing variable numbers of EGF receptors (Table 2). The titers of viruses carrying EMO envelopes were reduced up to 1000-fold by EGF.R expression and there was a correlation between the density of EGF receptor expression and the magnitude of reduction in virus titre (Table 2B). When NR6-hEGF.R cells were pre-treated with rEGF, which down-regulates EGF.R as confirmed by antibody staining (not shown), titers of viruses coated with EGF-fusion envelopes were greatly enhanced, reaching the range of titers obtained on parental NR6 cells (Table 2A). These data confirm that interaction of virions with EGF receptors leads to their sequestration into an abortive entry pathway that does not lead to membrane fusion or cytoplasmic release of the viral cores.

Host range and competitive sequestration of viruses carrying EA envelopes

Table 1A shows that viruses incorporating EA envelopes can infect NIH3T3 mouse fibroblasts through the amphotropic MLV receptor. When titrated on a panel of human cell lines expressing varying densities of EGF receptors, the EA virus showed a selective inability to infect all of the EGF receptor-positive human cells in the panel (Table 1B). However, they could easily infect human B and T cell lines (K422 and Jurkat) which are devoid of EGF.R and are presumably infected through the amphotropic receptor (Table 1). These data suggested that the EA viruses were efficiently sequestered by EGF.R expressed on human cells and to confirm their competitive sequestration, they were tested on parental and EGF receptor-expressing NR6 mouse fibroblasts (Table 2A). EGF receptor expression on NR6 cells led to a competitive inhibition (100-fold) of viral infection which was reversible when the NR6 transfectants were pre-treated with EGF to block/downregulate their EGF receptors.

Some sequestered virus can be rescued into an infectious entry pathway

After binding to receptor, EGF induces receptor dimerisation and its signal transduction, followed by ligand-receptor internalisation and routing to lysosomes, where EGF—EGF receptor complexes are degraded (Carpenter & Cohen, 1990 J Biol Chem 265 p7709–7712). We suspected that viruses bound to EGF receptors might therefore be rapidly internalised into the cell and routed to lysosomes for degradation. When EMO-carrying viral particles were used to infect A431 cells treated with the inhibitor of lysosomal degradation, chloroquine, a significant increase of infectivity (by approximately 2 logs) was obtained (Table 3). This effect was specific to EGF.receptors as EGF.receptor negative cells, such as K422 cells, did not respond similarly (Table 3).

Materials and Methods

Cell lines

TELCeB6 cell line was derived from the TELac2 line (Takeuchi et al, 1994 J Virol 68 p8001–8007) after transfection and clonal selection of cells containing a plasmid expressing MoMLV (Moloney murine leukemia virus) gag and pol proteins. TELCeB6 cells produce non-infectious viral core particles, carrying the MGFnlsLacZ reporter retroviral vector (Ferry et al, 1991 Proc Natl Acad Sci USA 88 p8377–8381). A431, TE671 (ATCC CRL8805), HT1080 (ATCC CCL121), EJ (Bubenik et al, 1973 Int. J. Cancer 11 p765–773) and EJ.A1, (an EJ clone that expresses ecotropic MLV receptors, Albritton et al, 1989 Cell 57 p659–666) were grown in DMEM (Gibco-BRL) supplemented with 10% fetal bovine serum (Gibco-BRL). K422 cells (Dyer et al, 1990 Blood 75 p709–714) and Jurkat T cells were grown in RPMI 1640 (Gibco-BRL) supplemented with 10% fetal bovine serum (Gibco-BRL). NR6 murine fibroblasts lacking detectable EGF receptors (Schneider et al, 1986 Proc Natl Acad Sci USA 83 p333–336) and NR6-EGF.R (an NR6 subclone obtained after transfection of a plasmid expressing the human epidermal growth factor receptor) cells were kindly provided by G. Gill (La Jolla, USA). psi2 cells (Mann et al, 1983 Cell 33 p153–159) and GP+EAM12 cells (Markowitz et al, 1988 Virol 167 p400–406) were derived from NIH-3T3 cells and express respectively MoMLV (ecotropic) and MLV-amphotropic envelopes which block the corresponding receptors (EcoR-1 and RAM-1) by interference. NIH3T3 clones transfected with EGF receptor expression constructs and expressing moderate or high levels of EGF receptors were kindly provided by Prof Thierry Velu (Erasmus Hospital, Brussels). NIH-3T3 and NIH-3T3-derived cell lines were grown in DMEM (Gibco-BRL) supplemented with 10% new born bovine serum (Gibco-BRL).

Chimeric envelopes

A PCR-derived DNA fragment encoding the 53 aa of hEGF (Bell et al, 1986 Nucleic Acids Res 14 p8427–8446) was generated using a cDNA template (ATCC 59957) and two primers:

```
OUEGF           5'-ATGCTCAGAGGGGTCAGTACGGCCCAGCCG
(Seq ID No 1)   GCCATGGCCAATAGTGACTCTGAATGTCC-3'
```

with an SfiI restriction site, and

```
OLEGF (Seq ID No 2) 5'-ACCTGAAGTGGTGGGAACTGCGCGC
                    GGCCGCATGTGGGGGTCCAGACTCC-3'
```

with a NotI site, and cloned after digestion with SfiI and NotI in either MoMLV SU for the EMO chimeric envelope or 4070A SU for the EA envelope (FIG. 1).

All envelope constructs were expressed as BglII-ClaI fragments (corresponding to positions 5408 and 7676 in MOMLV), cloned between BamHI and ClaI sites of the FBMOSALF expression vector (Cosset et al, submitted), in which a phleo selectable marker (Gatignol et al, 1988 FEBS Lett 230 p171–175) fused to the PGK (phospho-glycerate kinase) gene poly-adenylation sequence was introduced downstream to the C57 MLV LTR of FB3 (Battini et al, 1992 J Virol 66 p1468–1475).

Production of viruses

Envelope expression plasmids were transfected by calcium phosphate precipitation into TELCeB6 cells. Transfected cells were selected with phleomycin (50 mg/ml) and pools of phleomycin-resistant clones were used to harvest viruses from confluent cells after overnight incubation in DMEM and FBS (10%). These supernatants were used for ultracentrifugation to provide Western blot samples, for binding assays and for infection assays. Viruses (in 100 ml of producer cell supernatant) were also purified by gel-filtration on 2 ml columns (Bio-Rad) on a bed of S-1000 SEPHACRYL (Pharmacia). Fractions were obtained by elution with PBS at 4° C.

Immunoblots

Virus producer cells were lysed in a 20 mM Tris-HCl buffer (pH 7.5) containing 1% Triton-X100, 0.05% SDS, 5 mg/ml sodium deoxycholate, 150 mM NaCl, and 1 mM PMSF. Lysates were incubated for 10 min at 4° C. and were centrifuged for 10 min at 10,000×g to pellet the nuclei.

Supernatants were then frozen at −70° C. until further analysis. Virus samples were obtained by ultracentrifugation of viral supernatants (10 ml) in a SW41 Beckman Rotor (30,000 RPM, 1 hr, 4° C.). Pellets were suspended in 100 μl of PBS (phosphate buffered saline), and frozen at −70° C. Samples (30 mg for cell lysates, or 10 μl for purified viruses) were mixed in a 375 mM Tris-HCl (pH 6.8) buffer containing 6% SDS, 30% b-mercapto-ethanol, 10% glycerol, and 0.06% bromophenol blue, boiled for 3 min, then run on 10% SDS acrylamide gels. After protein transfer onto nitrocellulose filters, immunostaining was performed in TBS (Tris base saline, pH 7.4) with 5% milk powder and 0.1% TWEEN. Antibodies (Quality Biotech Inc, USA) were goat antisera raised against either RLV (Rausher leukemia virus) gp70-SU protein or RLV p30-CA protein, and were diluted 1/1,000 and 1/10,000, respectively. Blots were developed using HRPO-conjugated rabbit anti-goat antibodies (DAKO, UK) and an electrochemiluminescence kit (Amersham Life Science).

Binding assays

Target cells were washed in PBS and detached by a 10 min incubation at 37° C. with versene 0.02% in PBS. Cells were washed in PBA (PBS with 2% FCS and 0.1% sodium azide). $10^6$ cells were incubated with viruses for 30 min at 4° C. Cells were then washed with PBA and incubated in PBA containing 1/200 of RLV gp70 immune serum for 30 min at 4° C. Cells were washed twice with PBA and incubated with rabbit anti-goat FITC-conjugated antibodies (DAKO, U.K.). 5 min before the two final washes in PBA, cells were stained with 20 mg/ml propidium iodide. Fluorescence of living cells was analysed with a fluorescent-activated cell sorter (FACSCan, Beckton Dickinson). For hEGF.R staining, $10^6$ cells in 100 ml of PBA were incubated with 10 ml of anti-EGF.R antibodies (M886, DAKO, U.K.) for 30 min at 4° C.

Infection assays

Target cells were seeded in 24 multi-well plates at a density of $3\times10^4$ cells per well or in 6-multi-well plates at a density of $2\times10^5$ cells per well. Viral supernatant dilutions containing 4 mg/ml polybrene were added and cells were incubated for 3–5 hrs at 37° C. Viral supernatant was then removed and cells were incubated in regular medium for 24–48 hrs. X-Gal staining was performed as previously described (Takeuchi et al, 1994 J Virol 68 p8001–8007).

To block EGF.R, target cells were incubated 30 min at 37° C. in a medium containing $10^{-6}$ M rEGF (236-EG, R&D Systems, U.K.). Cells were then washed and infections were carried out as previously described. To block lysosomal acidification, 100 mM chloroquine phosphate (Sigma, U.K.) was added to the medium for 6 hr from the start of the infection protocol after which the cells were washed and incubated in regular medium.

TABLE 1

Infection by virions expressing targeting envelopes

A. On mouse fibroblasts[b]

| env[a] | 3T3 | 3T3/E | 3T3/A |
|---|---|---|---|
| A | $10^7$ | $10^7$ | $10^2$ |
| MO | $10^7$ | <1 | $10^7$ |
| EMO | $10^5$ | <1 | $10^5$ |
| EA | $10^6$ | nd | $10^1$ |

TABLE 1-continued

Infection by virions expressing targeting envelopes

B. On human cell lines[b]

| env[a] | A431 | HT108 | TE671 | K422 | Jurkat | EJ | EJ.A1 |
|---|---|---|---|---|---|---|---|
| EGFR | ++++ | ++ | + | − | − | ++ | ++ |
| A | $10^7$ | $10^7$ | $10^7$ | $10^5$ | $10^4$ | $10^6$ | $10^6$ |
| MO | <1 | <1 | <1 | <1 | <1 | <1 | $10^6$ |
| EMO | <1 | <1 | <1 | <1 | <1 | <1 | <1 |
| EA | <1 | <1 | $10^1$ | $10^4$ | $10^3$ | <1 | <1 |

[a]: envelope expressed on lacZ virions
[b]: titres as lacZ-EFU/ml. Abbreviations for cell lines: 3T3: NIH3T3; 3T3/E: psi2; 3T3/A: GP + EAM12

TABLE 2

Inhibition of infection by EGF.R

A. NR6 cells[b]

| env[a] | NR6. titre | NR6-wt hEGF.R. − rEGF[c] titre | NR6-wt hEGF.R. + rEGF[c] titre |
|---|---|---|---|
| MO | $1 \times 10^5$ | $5 \times 10^5$ | $5 \times 10^5$ |
| EMO | $5 \times 10^4$ | $1 \times 10^3$ | $10^5$ |
| A | $7 \times 10^4$ | $2 \times 10^5$ | $2 \times 10^5$ |
| EA | $2 \times 10^5$ | $3 \times 10^3$ | $5 \times 10^5$ |

B. NIH3T3 cells[b]

| EGFR No. / env[a] | 10,000 titre | 80,000 titre | 400,000 titre |
|---|---|---|---|
| MO | $10^6$ | $10^6$ | $10^6$ |
| EMO | $10^5$ | $10^4$ | $10^3$ |

[a]: envelope expressed on lacZ virions
[b]: titers as lacZ-EFU/ml.
[c]: cells were (+) or were not (−) pre-incubated with $10^{-6}$ M recombinant EGF for 30 min at 37° C.

TABLE 3

Effect of chloroquine on infection

| env[a] | NIH3T3[b]. − | NIH3T3[b]. + | A431[b]. − | A431[b]. + | TE671[b]. − | TE671[b]. + | K422[b]. − | K422[b]. + |
|---|---|---|---|---|---|---|---|---|
| MO | $10^6$ | $5 \times 10^5$ | <1 | 6 | <1 | 1 | <1 | <1 |
| EMO | $10^5$ | $5 \times 10^4$ | 1 | 225 | <1 | 46 | <1 | <1 |

[a]: envelope expressed on lacZ virions
[b]: titres as lacZ EFU/ml. Cells were treated (+) or not (−) with chloroquine.

OTHER EMBODIMENTS

Other embodiments will be evident to those of skill in the art. It should be understood that the foregoing detailed description is provided for clarity only and is merely exemplary. The spirit and scope of the present invention are not limited to the above examples, but are encompassed by the following claims.

We claim:

1. A recombinant viral particle for delivering a nucleic acid to a mammalian target cell, said particle comprising a member of a first specific binding pair that binds to a first receptor expressed on the surface of a target cell so as to cause infection thereof, and a surface-exposed member of a second specific binding pair that binds to a second receptor not expressed on the target cell and is expressed on a non-target cell to which the nucleic acid is not to be delivered, such that binding of the viral particle to the second receptor on a non-target cell via the member of the second specific binding pair inhibits infection of the non-target cell by the viral particle.

2. The recombinant viral particle of claim 1, wherein the viral particle is a retrovirus.

3. The viral particle of claim 1, wherein the member of the second specific binding pair binds to the human EGF receptor.

4. The viral particle of claim 1, wherein the member of the second specific binding pair comprises a portion of human EGF.

5. The viral particle of claim 1, wherein the member of the second specific binding pair comprises amino acids 1–53 of human EGF.

6. The viral particle of claim 1, wherein the member of the second specific binding pair has a high affinity (<$10^{-8}$M) for the second receptor.

7. The viral particle of claim 1, said particle being a recombinant MLV retroviral particle.

8. The viral particle of claim 1, wherein the member of the second specific binding pair is present as a fusion with the member of the first specific binding pair.

9. The retroviral particle of claim 8, wherein the member of the second specific binding pair is present as an N-terminal fusion with the retroviral env protein.

10. The viral particle of claim 1, wherein the member of the second specific binding pair binds to a second receptor which is expressed by cells which are capable of migration within the human body.

11. The viral particle of claim 10, wherein the second receptor is expressed by haemopoietic cells or transformed cells.

12. A composition comprising a recombinant viral particle of claim 1, and one or more cells to which the nucleic acid is delivered by the viral particle.

13. The composition of claim 12, wherein one or more cells to which the nucleic acid is delivered express the first receptor but not the second receptor, and one or more cells express both the first receptor and the second receptor.

14. The composition of claim 12, comprising haemopoietic cells.

15. A method of providing a viral particle having a restricted host range by providing a particle comprising a member of a first specific binding pair that binds to a first receptor expressed on the surface of a target cell so as to cause infection thereof, and a surface-exposed member of a second specific binding pair that binds to a second receptor not expressed on the target cell and is expressed on a non-target cell to which the nucleic acid is not to be delivered, such that binding of the viral particle to the second receptor on a non-target cell via the member of the second specific binding pair inhibits infection of the non-target cell by the viral particle.

16. The method of claim 15, resulting in the production of a recombinant viral particle of claim 1.

17. A method of providing a retroviral particle having an extended host range, wherein the retroviral particle comprises a nucleic acid for delivery to a target cell, the method comprising providing a retroviral particle having on its surface a member of a specific binding pair that binds to a cell surface receptor, wherein said binding reaction does not facilitate infection of the cell by the virus in the absence of an exogenously added substance, but does facilitate infection of the cell by the virus in the presence of an exogenously added substance that interferes with lysosomal-mediated inhibition of infection.

18. The method of claim 17, performed on a retroviral particle which, prior to performance of the method, does not infect a mammalian cell with which it is contacted or a particular mammalian cell type but which, after performance of the method, infects a mammalian cell or particular cell type with which it is contacted.

19. The method of claim 18, wherein the exogenously added substance is chloroquine.

* * * * *